United States Patent [19]

Hardman et al.

[11] Patent Number: 4,458,088
[45] Date of Patent: Jul. 3, 1984

[54] CONTINUOUS PROCESS FOR THE EXTRACTION AND ESTERIFICATION OF CARBOXYLIC ACID

[75] Inventors: Harley F. Hardman, Lyndhurst; John G. Frye, Jr., Euclid; Terry J. Mazanec, Solon, all of Ohio

[73] Assignee: The Standard Oil Company (Sohio), Cleveland, Ohio

[21] Appl. No.: 364,387

[22] Filed: Apr. 1, 1982

[51] Int. Cl.³ ............................................. C07C 67/10
[52] U.S. Cl. ............................. 560/96; 260/410.9 R; 560/204; 560/205; 560/217; 560/234; 560/265; 560/80; 560/103
[58] Field of Search ............... 260/410.9; 560/96, 100, 560/205, 217, 234, 265, 103, 129, 204, 80

[56] References Cited

U.S. PATENT DOCUMENTS

| | | | |
|---|---|---|---|
| 3,293,283 | 12/1966 | Dobson et al. | 560/217 |
| 3,328,439 | 6/1967 | Hamilton | 260/410.9 |
| 3,354,199 | 11/1967 | Lachowicz et al. | 560/205 |
| 3,714,234 | 1/1973 | White | 560/217 |
| 3,784,573 | 1/1974 | Fields et al. | 260/346.3 |
| 4,074,062 | 2/1978 | Murakani et al. | 560/217 |
| 4,112,235 | 9/1978 | Schmerling | 560/100 X |
| 4,117,238 | 9/1978 | Ackermann et al. | 560/217 |
| 4,202,990 | 5/1980 | Murakani et al. | 560/217 |
| 4,205,182 | 5/1980 | Izumi et al. | 560/247 |
| 4,228,084 | 10/1980 | Ackermann et al. | 260/348.12 |
| 4,280,009 | 7/1981 | Erpenbach et al. | 560/205 |
| 4,280,010 | 7/1981 | Erpenbach et al. | 560/205 |

Primary Examiner—Natalie Trousof
Assistant Examiner—Vera C. Clarke
Attorney, Agent, or Firm—D. L. Pawl; D. J. Untener; L. W. Evans

[57] ABSTRACT

A continuous process for the production of alkyl esters from carboxylic acids wherein an aqueous stream containing a first carboxylic acid, $RCO_2H$, is contacted with an organic stream comprising a carboxylic acid ester, $R''CO_2R'$, so that the organic stream is enriched with $RCO_2H$. The $RCO_2H$ enriched organic stream is separated from the aqueous stream and is contacted with a catalyst to obtain a second carboxylic acid, $R''CO_2H$, and a product carboxylic acid ester, $RCO_2R'$. The product ester, $RCO_2R'$, is separated from the second acid, $R''CO_2H$, the reactant ester, $R''CO_2R'$, and the first acid, $RCO_2H$, and the second acid, $R''CO_2H$, is esterified to obtain the reactant ester, $R''CO_2R'$, which is recycled to the initial part of the process. In this process R is aliphatic or aromatic, R' is alkyl and R" is aliphatic with at least about 4 carbon atoms. When the reactant ester is a bifunctional polymer having both sulfonic acid and R' carboxylic acid ester pendant functional groups, this process may be performed in the absence of a catalyst.

39 Claims, 1 Drawing Figure

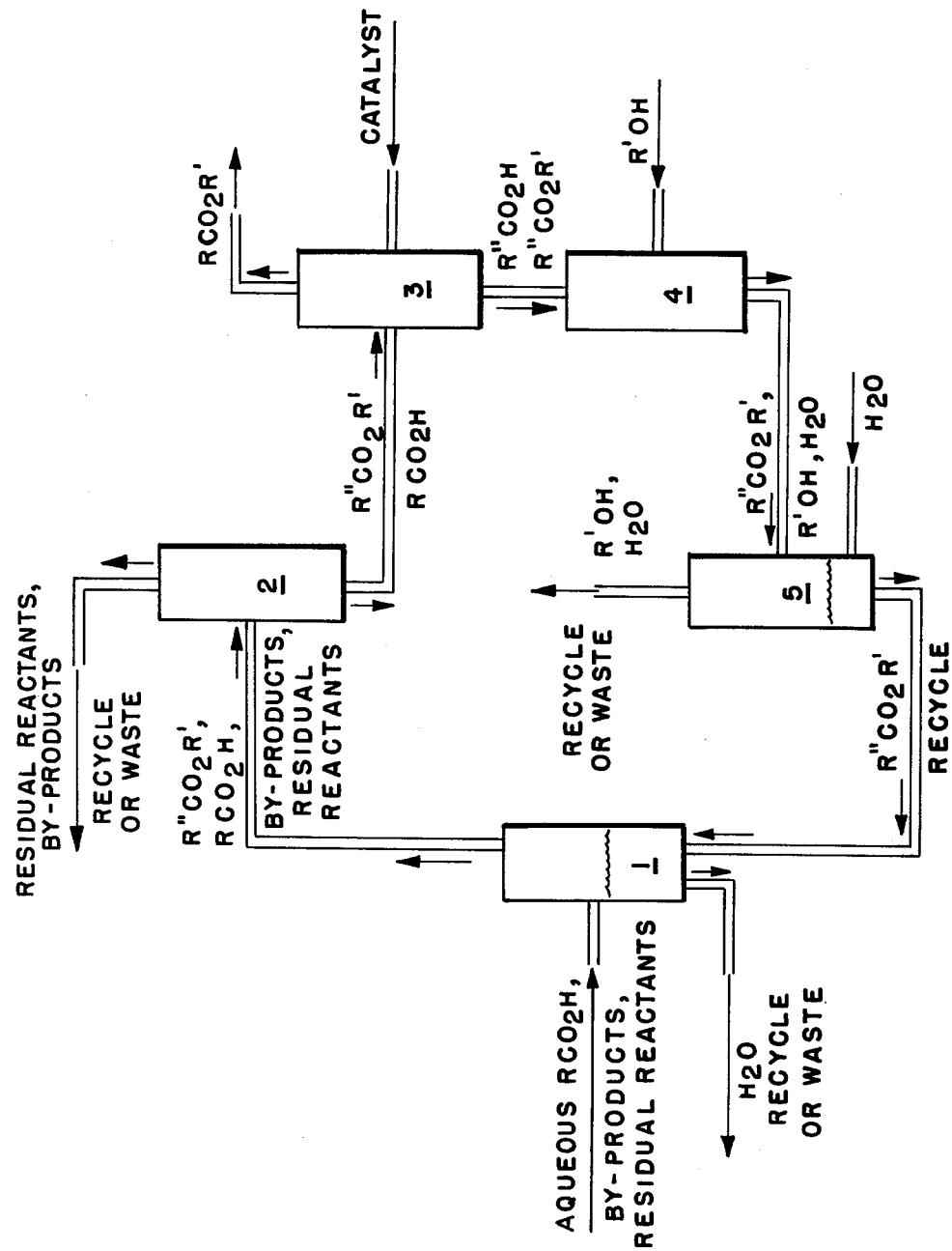

CONTINUOUS PROCESS FOR THE EXTRACTION AND ESTERIFICATION OF CARBOXYLIC ACID

BACKGROUND OF THE INVENTION

1. Field of the Invention

This invention relates to a continuous process for the extraction and esterification of carboxylic acids. More specifically, this invention relates to a process for the extraction of a first carboxylic acid, denoted $RCO_2H$, from an aqueous stream into an organic stream. This organic stream may comprise a carboxylic acid ester reactant, denoted $R''CO_2R'$. The ester reactant, $R''CO_2R'$, and the first acid, $RCO_2H$, are contacted with a catalyst to form a product carboxylic acid ester, denoted $RCO_2R'$, and a second carboxylic acid, denoted $R''CO_2H$. The reactant ester, $R''CO_2R'$, is regenerated by esterifying the second acid, $R''CO_2H$. The reactant ester, $R''CO_2R'$, is then recycled to the process. In this process R is aliphatic or aromatic, R' is alkyl and R'' is aromatic or aliphatic having at least about 4 carbon atoms. Where the ester reactant is a bifunctional polymer, having both sulfonic acid and R' carboxylic acid ester pendant functional groups, this process can be performed in the absence of a catalyst.

2. Description of the Prior Art

Carboxylic acid esters have many diverse uses. Many aromatic and alkyl esters are useful in perfumes and artificial flavorings. For example, methyl butyrate and ethyl butyrate are used in the formation of artificial rums. Some carboxylic acid esters are also used as solvents in varnishes, lacquers and paints. Some carboxylic acid esters, particularly those formed from unsaturated acids, may be reacted further to form polymers useful in the manufacture of fibers and coatings or films.

Conventionally, esters can be formed by either a batch or a continuous process. While a continuous process is preferred for commercial operations, it is often impracticable due to problems in product separation.

Carboxylic acid esters can be formed using one of several reaction pathways. One pathway is ester alcoholysis, depicted below:

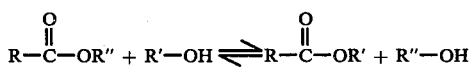
(I)

The reactant ester, $RCO_2R''$, is reacted with an alcohol, $R'OH$, usually in the presence of a catalyst. The reaction results in the transfer of the R' group to the ester, followed by cleavage of the R'' group to yield a product ester of the general formula $RCO_2R'$ and an alcohol, $R''OH$.

A second possible pathway involves the reaction of an acid with an ester. This reaction, called "ester acidolysis", can be represented as follows:

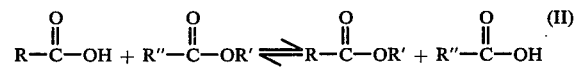
(II)

In this reaction R' is transferred from the reactant ester, $R''CO_2R'$, to the first acid, $RCO_2H$. This results in a product ester of the general formula $RCO_2R'$ and a second acid, $R''CO_2H$.

Esters may also be formed by the addition of an alcohol to an organic acid. This process, depicted below in Reaction III, results in the transfer of the alcohol to the organic acid with $H_2O$ as a by-product:

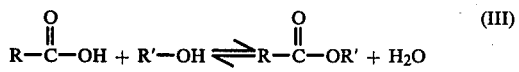
(III)

In many known commercial operations for producing carboxylic acids the product is recovered from the reactor in a dilute aqueous solution. Since most esterification reactions require that the reactants be in concentrated form, extra steps are required to concentrate the carboxylic acid from a product stream before the acid can be introduced to an esterification process. These extra steps, such as distillation, are often expensive, may result in product losses and impede a smooth coupling of the esterification process with the process producing the carboxylic acid.

Esterification reactions usually involve a reversible equilibrium which can be driven forward by removal of one or more of the products. In a continuous process, product removal is frequently accomplished by product distillation. Alcoholysis (Reaction I), acidolysis (Reaction II) or addition of alcohol to an organic acid (Reaction III), however, frequently give rise to azeotropic mixtures. For example, when acrylic acid is esterified by ethanol according to reaction III the reaction products are ethylacrylate and water. A ternary azeotrope is formed by the combination of ethanol, ethylacrylate and water. Therefore, when distillation is executed an extra step must be performed to separate ethylacrylate from the azeotrope. This makes the process more time consuming and expensive than if the ester could be distilled as an isolated product. Also, when an azeotrope is formed involving a product and a reactant and the azeotrope is continuously removed, the effect of product removal on the position of the equilibrium is at least partially negated by the simultaneous removal of one of the reactants.

U.S. Pat. No. 4,280,009 to Erpenbach discloses a continuous process for the production of 2-ethylhexylacrylate free from dioctylether. U.S. Pat. No. 3,354,199 to Lachowicz discloses a process for the production of ethylacrylate by reacting acrylic acid with ethanol in the presence of a catalyst and entrainer to produce ethylacrylate and water.

U.S. Pat. No. 4,280,010 to Erpenbach discloses a continuous process for the production of alkylacrylates free of ether by the reaction of acrylic acid or methacrylic acid with an alcohol in the presence of a catalyst to form an alkylacrylate and water.

U.S. Pat. No. 4,117,238 to Ackermann involves a process for the transesterification of acrylic and methacrylic esters according to reaction I wherein acrylic or methacrylic esters are reacted with alcohols in the presence of an alkali metal cyanide. U.S. Pat. No. 4,228,084, also to Ackermann, involves a similar process for the production of glycidylmethacrylate from methylmethacrylate and glycidol.

U.S. Pat. No. 4,074,062 to Murakami discloses a process for producing unsaturated carboxylic acid esters by reacting unsaturated carboxylic acids with alcohols in the presence of a catalyst. U.S. Pat. No. 4,202,990 to Murakami involves a process for producing unsaturated carboxylic acid esters by following the reaction steps for Murakami U.S. Pat. No. 4,074,062 using a catalyst consisting of chelate compounds of zirconium and/or calcium instead of the barium, thallium or molybdenum compounds of U.S. Pat. No. 4,074,062.

U.S. Pat. Nos. 3,293,283 to Dobson, 3,328,439 to Hamilton, 3,714,234 to White, 3,784,537 to Fields, 4,112,235 to Schmerling, and 4,205,182 to Izumi disclose esterification processes similar to those described above.

SUMMARY OF THE INVENTION

It is the object of the present invention to provide a continuous process for the production of alkyl esters from carboxylic acids.

It is the further object of the present invention to provide a continuous process for the production of alkyl esters from carboxylic acids which permits the continuous removal of the product ester in an isolated form.

In addition, it is the object of the present invention to provide a continuous process for the production of alkyl esters from carboxylic acids which can utilize a dilute feed stream.

Additional objects, advantages and novel features of the invention will be set forth in part of the description which follows, and in part will become apparent to those skilled in the art upon examination of the following or may be learned by practice of the invention. The objects and advantages of the invention may be realized and attained by means of the instrumentalities and combinations particularly pointed out in the claims.

To achieve the foregoing and other objects and in accordance with the present invention, as embodied and broadly described herein, the process of this invention may comprise:

(a) contacting an aqueous stream containing a first carboxylic acid, $RCO_2H$, with an organic stream comprising a reactant carboxylic acid ester, $R''CO_2R'$, so that the organic stream is enriched with $RCO_2H$;

(b) separating the aqueous stream from the $RCO_2H$ enriched organic stream;

(c) contacting the organic stream of (b) with a catalyst to obtain a product carboxylic acid ester, $RCO_2R'$, and a second carboxylic acid, $R''CO_2H$;

(d) separating the product ester, $RCO_2R'$, from the second carboxylic acid, $R''CO_2H$;

(e) esterifying the second acid, $R''CO_2H$, to regenerate the reactant ester, $R''CO_2R'$; and (f) recycling the reactant ester, $R''CO_2R'$, to (a).

Where the reactant ester, $R''CO_2R'$, is a solid the organic stream comprises a solvent which is subsequently contacted with the reactant ester, $R''CO_2R'$, to obtain the product ester, $RCO_2R'$ and the second carboxylic acid, $R''CO_2H$. The second acid, $R''CO_2H$, is then re-esterified and recycled to step (c).

In this process, R is aliphatic or aromatic, R' is alkyl, and R'' is aromatic or aliphatic having at least about 4 carbon atoms. Also, when the ester reactant is a bifunctional polymer having both sulfonic acid and carboxyl pendant functional groups, wherein the carboxyl pendant functional groups comprise R' carboxylic acid esters, the above process may be performed without the use of a catalyst.

In accordance with the objects and purposes stated above, a further aspect of the present invention may also comprise the esterification of a carboxylic acid, $RCO_2H$, wherein R is aryl, alkyl or alkenyl, R' is alkyl having about 8 or less carbon atoms, and where R'' is aromatic or aliphatic having at least about 4 carbon atoms.

It is preferred that the boiling point of the product ester, $RCO_2R'$, be lower than the boiling point of the first acid, $RCO_2H$, the reactant ester, $R''CO_2R'$, and the second acid, $R''CO_2H$. When this occurs, it may be preferred to separate $RCO_2R'$ from $RCO_2H$, $R''CO_2R'$ and $R''CO_2H$ by distillation.

As embodied, broadly described and claimed herein the present invention, by accomplishing the foregoing and other objects, achieves a continuous process for the production of alkyl esters from carboxylic acids which permits continuous removal of a product ester in an isolated form, thereby shifting the reaction equilibrium forward while simultaneously providing an unadulterated product.

It is a further accomplishment of the present invention to provide a continuous process for the production of alkyl esters from carboxylic acids which can utilize a dilute feed stream, thereby obviating the need to concentrate feed streams prior to introduction to an esterification reaction vessel and permitting operation of an esterification process continuous with a process producing the components of the feed stream.

BRIEF DESCRIPTION OF THE DRAWING

The invention is hereinafter described in reference to the accompanying drawing in which the FIGURE is a diagrammatic representation of the preferred embodiment of the present invention.

DETAILED DESCRIPTION

Many methods of forming carboxylic acids involve use of an aqueous reaction medium and/or use of reaction pathways which result in the production of significant amounts of $H_2O$. For example, when methacrylic acid is produced by the oxidation of isobutyraldehyde, the molar ratio of methacrylic acid to by-product water is 1:1.

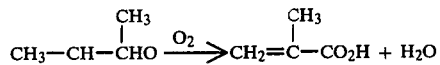

This process is also accompanied by the production of other waste products, such as carbon monoxide and carbon dioxide. The product stream is also often diluted by steam which is co-fed as a diluent and by water used to increase product recovery by "scrubbing" the effluent gas.

Our preferred embodiment which is preferred due to its immediate applicability to commercial processes, contemplates that the acid reactant used in the present invention, denoted $RCO_2H$ where R is aliphatic or aromatic, is produced under substantially aqueous conditions, the product stream possibly containing various residual reactants and by-products as well as the product acid, $RCO_2H$. As shown in the accompanying FIGURE depicting the preferred embodiment, in step (1) of the present invention the reactant or first carboxylic acid, $RCO_2H$, is transferred from the aqueous phase to the organic stream by contacting the aqueous stream with an organic stream comprising an ester reactant, $R''CO_2R'$, wherein R' is alkyl and R'' is aromatic or aliphatic with at least 4 carbon atoms, so that the organic stream becomes enriched with $RCO_2H$.

Although a desired amount of $RCO_2H$ may be transferred from the aqueous stream to the organic stream by contacting it with only one portion of the organic stream, the aqueous stream may be contacted serially with more than one portion of fresh organic stream until the desired amount of acid has been transferred. Although these serial contacts with the organic stream can be performed using a batch mode, it is preferred that they be continuous.

Preferably the first carboxylic acid, $RCO_2H$, and the reactant carboxylic acid ester, $R''CO_2R'$, are chosen so that the organic stream is capable of being enriched with a substantial amount of the $RCO_2H$ from the aqueous stream, thereby minimizing the number of portions of the organic stream with which the aqueous stream must be contacted in order to remove a given percentage of the acid, $RCO_2H$, from the aqueous stream. It is preferred that $RCO_2H$ be chosen so as to have an $R''CO_2R'/H_2O$ solubility ratio of at least 1. This ratio is defined by the general formula:

$$X = (S_a/S_b)$$

wherein
$S_a$ = solubility of X in substance "a"; and
$S_b$ = solubility of X in substance "b".

It is also preferred that the concentration of the acid, $RCO_2H$, in the aqueous stream be at least 15% by weight in order to minimize the quantity of organic stream the aqueous stream must be exposed to in order to achieve transfer of a predetermined percentage of the acid to the organic stream. While the molar ratio of the reactant ester, $R''CO_2R'$, to the first carboxylic acid, $RCO_2H$, may be about 1:1 to 20:1, it is preferred that the ratio be about 5:1 to 10:1.

It is required in the preferred embodiment that the reactant ester, $R''CO_2R'$, be essentially immiscible with water so that the aqueous stream and the organic stream form separate phases. This enables separation of the aqueous stream from the organic stream by conventional physical means such as gravity separation. It is also contemplated in the preferred embodiment that the first acid, $RCO_2H$, and the reactant ester, $R''CO_2R'$, are liquids.

After the aqueous stream has been contacted with the organic stream the two streams are separated by conventional means such as gravity separation. The aqueous portion is either recycled to the $RCO_2H$ producing process or is discharged as waste. The organic stream, which comprises $RCO_2H$ and $R''CO_2R'$ and may contain by-products and residual reactants transferred from the aqueous stream, may then optionally proceed to step (2) before proceeding to step (3).

By-products and residual reactants in the aqueous stream which are extracted into the organic stream along with the acid can be removed from the organic stream in step (2) by conventional methods. Step (2), however, is optional and the preferred embodiment contemplates the possibility of the organic stream passing directly to step (3) after separation of the organic stream from the aqueous stream in step (1). Removal of by-products and residual reactants from the $RCO_2H$ producing process if often desired, however, to prevent their reaction with the components of the present process and thereby yielding undesired products. For example, commercial operations for the production of methacrylic acid commonly produce isobutyric acid and acetone as by-products. Although IBA and acetone are extracted into the organic stream of the present invention, both of these substances are readily removed by distillation. Although removal of by-products and residual reactants can occur at several points in the present process, it is preferred that removal of by-products and residual reactants occur after the aqueous stream has been separated from the organic stream in step (1) and before the organic stream is contacted with the catalyst in step (3) to minimize the reaction of these by-products or residual reactants with the components of the present process.

Preferably a polymerization inhibitor is added to the organic stream before it is contacted with the catalyst in step (3) to prevent polymerization of the first acid, $RCO_2H$, the reactant ester, $R''CO_2R'$, the second acid, $R''CO_2H$, or the ester product, $RCO_2R'$. This inhibitor is most useful when the first acid, $RCO_2H$, or the reactant ester, $R''CO_2R'$, is unsaturated since polymerization occurs more readily with unsaturated compounds. This inhibitor may be any one of a number of compounds generally known to inhibit polymerization. Examples of suitable inhibitors are alkyl nitroso compounds, such as nitroso butane, quinones, such as hydroquinone, or thiazine compounds, such as phenothiazine.

Subsequent to the organic stream being separated from the aqueous stream in step (1), the organic stream is contacted with a catalyst in step (3) to obtain a product carboxylic acid ester, $RCO_2R'$, and a second carboxylic acid, $R''CO_2H$. This reaction is represented in reaction II above.

The catalyst may be either a strong acid of pKa of about 2.0 or less, such as $H_2SO_4$ or HCl, a metal salt which is a Lewis acid, such as $SnCl_2$, or a strong base with a pKa of about 10.0 or more, such as KOH or NaOH. While the catalyst may be a soluble compound, such as $H_2SO_4$, it is preferred that the catalyst be a resin which is a highly stable, insoluble matrix capable of carrying functional groups, due to the ease of recovering a resin from the reaction mixture. Preferably this resin is a perfluoro sulfonic acid polymer, such as acid exchanged Nafion-501 or Nafion-511, (obtainable from E. I. du Pont) or a phenyl sulfonic acid on polystyrene, such as Dowex 50 (obtainable from the Dow Chemical Company).

The product ester, $RCO_2R'$, is separated from the reaction mixture in step (3). This may occur after the esterification reaction has reached equilibrium and the reaction terminated. It is preferred, however, that separation of $RCO_2R'$ occur continuously during the reaction, thereby causing a forward shift of the reaction equilibrium by removal of one of the reaction products as well as achieving isolation of the desired ester.

Preferably the product ester, $RCO_2R'$, is separated from the reaction mixture, including $R''CO_2H$, $R''CO_2R'$, and $RCO_2H$ and the catalyst, by distillation. Therefore, in order to obtain $RCO_2R'$ isolated in the distillate, it is preferred that the boiling point of $RCO_2R'$ be lower than the boiling points of $R''CO_2H$, $R''CO_2R'$ and $RCO_2H$. While only a small difference in boiling points is required, it is preferred that the boiling point of $RCO_2R'$ be at least 10° C. lower than the boiling point of any of the other reaction components. Also, a salt, such as $NH_4HSO_4$, may be added to the reaction mixture in about 1 to 30% by weight to facilitate separation of $RCO_2R'$ via distillation by causing increased ionic strength in the reaction mixture. When the product ester is continuously distilled, the temperature at which step (3) is performed will be determined by the boiling point of the product ester.

Separation of the product ester, $RCO_2R'$, from the reaction mixture in step (3) results in a residue comprising the second carboxylic acid, $R''CO_2H$, and the catalyst and may also contain by-products from the esterification reaction. Since the preferred embodiment contemplates that a molar excess of the reactant ester, R″CO$_2$R′, will be present in the reaction mixture, the residue from step (3) may also contain unreacted R″CO$_2$R′. The second acid, R″CO$_2$H, optionally accompanied by the catalyst, excess R″CO$_2$R′, and esterification by-products, is re-esterified in step (4) to obtain the reactant ester, R″CO$_2$R′. Preferably an alcohol is used as the re-esterification agent which donates R′ to the second acid, R″CO$_2$H, according to reaction III. When an alcohol is used as the esterification agent the molar ratio of alcohol to second acid, R″CO$_2$H is preferably about 2:1 to 30:1.

Many commonly known compounds are capable of catalyzing the re-esterification of R″CO$_2$H by an alcohol, including those disclosed above as catalyzing the esterification reaction in step (3). Although use of a catalyst is preferred, under certain conditions this re-esterification reaction may proceed in the absence of a catalyst. Due to ease of operation it is preferred that the re-esterification catalyst be the same catalyst as that utilized in step (3) since this obviates the need to separate the catalyst of step (3) from the reaction mixture before the re-esterification reaction is performed in step (4).

The regenerated reactant ester, R″CO$_2$R′, and the re-esterification agent are then separated from each other in step (5) by conventional extraction and/or distillation techniques. When an alcohol is used as the re-esterification agent extraction with H$_2$O is preferred due to the high solubility of many alcohols in water. The regenerated reactant ester, R″CO$_2$R′, is then recycled to step (1) of the process.

A variety of aliphatic and aromatic acids can be used as RCO$_2$H in the practice of the present invention. It is preferred, however, that R be aryl, alkyl, or alkenyl. When R is aryl, however, it is preferred that RCO$_2$H be an aryl acid with at least two acid functions. When RCO$_2$H is an aryl acid with at least 2 acid functions, it is further preferred that RCO$_2$H also comprise a compound with at least 2 fused aromatic rings such as 5,8-dibromonaphthalene-2,3-dicarboxylic acid.

When R is alkyl, it is preferred that RCO$_2$H be a branched or straight chain alkyl acid with R having about 6 or less carbon atoms, such as 2,3-dimethylvaleric acid, 2-methylbutyric acid, n-butyric acid, isobutyric acid, propanoic acid or acetic acid.

RCO$_2$H may also be a branched or straight chain alkenyl acid such as 3-methyl-2-butenoic acid or 3-hexenoic acid. It is preferred, however, when R is alkenyl that RCO$_2$H be an alkenyl acid with an unsaturated bond in the alpha position, such as 2-methyl-2-butenoic acid. It is further preferred that when R is alkenyl, that RCO$_2$H be an alkenyl acid with R having about 10 or less carbon atoms, such as acrylic acid or methacrylic acid, in order to facilitate separation of the product ester, RCO$_2$R′, from the reaction mixture.

Preferably R′ is alkyl with about 8 or less carbon atoms and may be either linear or branched. Alkyl groups such as methyl, ethyl, propyl, butyl and 2-ethylhexyl are preferred.

R″ may be aliphatic or aromatic. It is preferred, however, that R″ be aliphatic with at least about 4 carbon atoms, and preferably with at least about 5 carbon atoms. Preferably R″ is selected so that R″CO$_2$R′ is an octanoic, benzoic, lauric or myristic acid. When R″ has about 6 or more carbon atoms the reactant ester, R″CO$_2$R′, can be a solid.

Although the preferred embodiment contemplates that the reactant ester, R″CO$_2$R′, is a liquid, the present invention can also be practiced when R″CO$_2$R′ is a solid ester, such as trimethyl 1, 3, 5-benzenetricarboxylate or carboxylated polystyrene.

When R″CO$_2$R′ is a solid under the conditions of step (1) the organic stream in the above described preferred embodiment comprises a solvent instead of the reactant ester, R″CO$_2$R′. Although many generally known organic solvents can be used, it is preferred that the solvent be an aromatic, such as toluene or xylene, or a saturated alkane, such as hexadecane. Further, it is required that RCO$_2$H and the solvent be liquids, and that the solvent be substantially immiscible in H$_2$O. In addition, it is preferred that the solvent be chosen so that the first acid, RCO$_2$H, has a solvent/H$_2$O solubility ratio of at least 1. It is also preferred that the reactant ester, R″CO$_2$R′, be soluble in the solvent, although solubility of R″CO$_2$R′ in the solvent is not required.

In the embodiment wherein R″CO$_2$R′ is a solid, the organic stream, which comprises a solvent, is contacted with the aqueous stream and is separated from the aqueous stream in step (1) as described above in the preferred embodiment. The organic stream may then be shunted directly to step (3) or may optionally undergo removal of by-products and residual reactants in step (2) as described in the preferred embodiment above. The organic stream is then contacted with the reactant ester, R″CO$_2$R′, and the catalyst in step (3) to obtain the product ester, RCO$_2$R′, and the second carboxylic acid, R″CO$_2$H. Steps 4 and 5 are performed as described in the preferred embodiment. Following regeneration of the reactant ester in step (5) the reactant ester, R″CO$_2$R′, is recycled to step (3).

To facilitate separation of the product ester, RCO$_2$R′, from the reaction mixture, it is preferred that the boiling point of RCO$_2$R′ be lower than the boiling points of R″CO$_2$H, R″CO$_2$R′, RCO$_2$H, the catalyst and the solvent.

Although the preferred embodiment contemplates use of a catalyst, the present invention can also be practiced without the use of a catalyst when the reactant ester is a bifunctional polymer which is capable of transfering an ester moeity to the first carboxylic acid, RCO$_2$H, as well as acting as a proton donor in the esterification reaction. This bifunctional polymer has a conventional polymeric backbone of carbon or carbon and at least one of oxygen or nitrogen, and has both sulfonic acid and carboxyl pendant functional groups, wherein the carboxyl pendant functional groups comprise R′ carboxylic acid esters. Preferably the sulfonic acid pendant groups comprise sulfonated phenyl pendant functional groups. The carboxyl pendant groups may comprise carboxylated phenyl pendant groups, although it is preferred that the carboxyl groups be attached directly to the polymeric backbone.

It is preferred that the ratio of carboxyl pendant groups to sulfonated phenyl pendant groups be about 1:1 to 4:1. This polymer may also contain carboxyl pendant groups which are in the acid rather that the ester form, and may be derived from the copolymerization of styrene with maleic anhydride. Possible bifunctional polymers are depicted below:

Carboxylated polystyrene

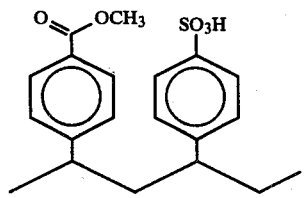

1/1 Maleic anhydride/styrene

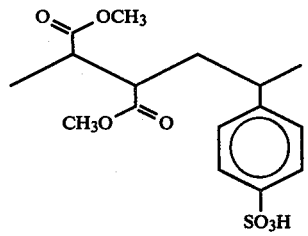

Due to the length of the polymer chains the bifunctional polymer is usually a solid. Therefore the embodiment which can be practiced without a catalyst usually utilizes the modifications for a solid ester set forth above. In step (3), however, the ester-containing, bifunctional polymer is contacted with the first acid, $RCO_2H$, contained in the organic stream to obtain the product ester, $RCO_2R'$, and an acidified bifunctional polymer resulting from cleavage of the carboxylic acid ester groups from the ester containing polymer. The acidified bifunctional polymer can be re-esterified using the procedures set forth above to obtain the ester-containing bifunctional polymer which is then recycled to step (3).

In the above described embodiments it is preferred that steps (1) and (2) of the present invention be performed at temperatures of about 0° to 100° C. and at pressures of about 0.01 to 10 atm. It is preferred that steps (3), (4) and (5) be performed at temperatures of about 50° to 200° C. and at pressures of about 0.001 to 10 atm.

SPECIFIC EMBODIMENTS

Example 1

An experiment was conducted to demonstrate the feasibility of extracting an organic acid into an organic ester. Accordingly, a 19.9% methacrylic acid in $H_2O$ solution was made and extracted serially at room temperature and atmospheric pressure with two volumes of methyloctanoate per extraction of one volume of aqueous solution. The methyl octanoate used for these extractions contained 2.2% by weight octanoic acid which was added to simulate the steady state condition of the reactant ester, $R''CO_2R'$, in a continuous process with 80% re-esterification of the second acid, $R''CO_2H$. The results of this experiment are summarized in Table I.

TABLE I

Successive Extractions of Methacrylic Acid from $H_2O$ by 2.2% Octanoic Acid in Methyl Octanoate

| Extraction | Water Phase % MAA of Total Charged | Organic Phase % MAA of Total Charged | Cumulative |
|---|---|---|---|
| Initial Sol'n | 100.0% | — | — |
| First | 7.5% | 86.9% | 86.9% |
| Second | 1.6% | 7.3% | 94.2% |
| Third | 2.5% | 3.4% | 97.6% |

Example 2

An experiment was conducted to demonstrate the feasibility of esterifying the first acid, $RCO_2H$, with the reactant ester, $R''CO_2R'$, and continuously distilling the product ester, $RCO_2R'$. Accordingly, 29.23 g methacrylic acid, 181.80 g methyl octanoate and 13.47 g Nafion-501 resin were combined in a 1.0 liter flask. Approximately 100 mg. of hydroquinone was also added as a polymerization inhibitor. The flask was heated at atmospheric pressure, during which a solution of hydroquinone in methyl octanoate was dripped into the reaction mixture. 28.63 g of methyl methacrylate, as identified by gas chromatography, was distilled continuously at an overhead temperature of about 75°–110° C. to give a methyl methacrylate yield of 85.29%.

Example 3

An experiment was performed to demonstrate the feasibility of re-esterifying the acid, $R''CO_2H$, to obtain the ester, $R''CO_2R'$. Octanoic acid, 23.4 g, was mixed with 48 g of methanol and 12 g of Nafion-501. Methyl octanoate, 106.6 g, was added to simulate the effluent of an acid esterification reactor. The mixture was refluxed at approximately 70° C. for 6 hours and then allowed to cool to room temperature. The mixture was then extracted three times with 200 ml $H_2O$ per extraction to remove water and any unreacted methanol. Gas chromatography of the organic layer revealed that 88% of the octanoic acid had been re-esterified to methyl octanoate.

Experiments were also performed to demonstrate that aliphatic or aromatic acids other than methacrylic acid can be extracted from an aqueous stream and esterified according to the present invention. The results of these experiments are summarized in Examples 4 and 5.

Example 4

An extraction experiment was run using a 30% by weight acrylic acid (AA) in water solution. 100 cc of this solution was extracted serially three times, with 50 cc of methyl octanoate used in each extraction. The results of this experiment are summarized in Table II.

TABLE II

| Extraction | Water Phase % AA of Total Charged | Organic Phase % AA of Total Charged | Extracted AA Cumulative |
|---|---|---|---|
| Initial Sol'n | 100.0% | — | — |
| First | 48.57% | 49.22% | 49.22% |
| Second | 19.42% | 26.90% | 76.12% |
| Third | 2.96% | 13.99% | 90.11% |

Example 5

An esterification experiment was performed by combining 131.76 g of methyl octanoate, 20.00 g of acrylic acid, 15 g of Nafion-511 resin and 0.5 g phenothiazine in a flask. The flask was heated with a heating mantle and stirred by a magnetic stirrer. The flask was heated slowly to a pot temperature of approximately 65° C. The product ester, methyl acrylate, was continuously distilled into a flask containing approximately 0.5 g of phenothiazine. A solution of phenothiazine in methyl octanoate was dripped into the distillation column to inhibit polymerization. When the pot temperature began to approach the boiling point of methyl octanoate, the distillation was terminated. A total of 23.46 g of distillate was obtained. Gas chromatography revealed this product to be 90.19% methyl acrylate. Thus this process resulted in a 88.57% yield of methyl acrylate based on the amount of acrylic acid charged to the reaction.

The experiment summarized in Example 6 was performed to demonstrate that saturated alkyl acids can be esterified and distilled according to the process of the present invention.

Example 6

Nafion-511, 15.12 g, 19.99 g of 99% isobutyric acid and 107.75 g of methyl octanoate were placed in a flask. The flask was heated by an electric mantle and stirred by a magnetic stirrer. The product was distilled at an overhead temperature of about 90° C. When the overhead temperature began dropping, the distillation was terminated. 22.35 g of organic product was obtained. Analysis by gas chromatography revealed that 22.08 g of methyl isobutyrate was contained in the distillation product, or 96.26% of the possible theoretical yield.

The experiment summarized in Example 7 was performed to demonstrate that the ester, R"CO$_2$R', can esterify an organic acid according to the present invention if R' is an alkyl with more than 1 carbon atom.

Example 7

An esterification experiment was performed by combining 143.43 g of ethyl octanoate, 20.00 g of acrylic acid, 15.0 g of Nafion-511, and approximately 1 g of phenothiazine in a flask. A 1% phenothiazine in ethyl octanoate solution was slowly dripped into the reaction mixture. The flask was heated with an electric mantle and stirred by a magnetic stirrer. The product was continuously distilled at an overhead temperature of approximately 63°–90° C. When the pot temperature reached 202° C., distillation was terminated. A total of 25.96 g of distillate was obtained. Ethyl acrylate was identified by boiling point as the product.

The experiment summarized in Example 8 was performed to demonstrate that a bifunctional polymer with both sulfonic acid and R' carboxylic acid ester pendant functional groups could serve as both a proton and R' group donor so that the process of the present invention could be performed without the use of a catalyst.

Example 8

A bifunctional polymer, depicted below, was prepared by reacting maleic anhydride/styrene 1:1 copolymer with methanol and concentrated H$_2$SO$_4$:

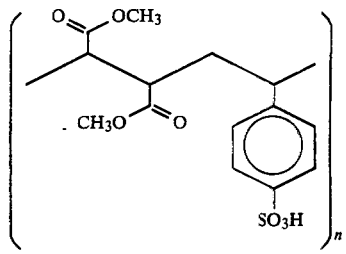

An organic solvent, diglycol methyl ether, 103.30 g, was combined with 3.95 g of methacrylic acid, 20.64 g of the bifunctional polymer, and 0.10 g of hydroquinone. This mixture was stirred and heated slowly up to 122° C. After heating at 122° C. for 1 hour, approximately 20% of the methacrylic acid had been converted to methyl methacrylate.

The foregoing description and examples have been presented for purposes of illustration and description. They are not intended to be exhaustive or to limit the invention to the precise form disclosed. Many other modifications and variations are possible in light of the above teaching, preferred embodiment, and other embodiments which were chosen and described in order to best explain the principles of the invention and its practical application to thereby enable others skilled in the art to be utilize the invention in various embodiments and with various modifications as are suited to the particular use contemplated. It is intended that the scope of the invention be defined by the following claims:

We claim:

1. A continuous process for the production of alkyl esters from carboxylic acids comprising:
   (a) contacting an aqueous stream containing a first carboxylic acid, RCO$_2$H, with an organic stream comprising a reactant carboxylic acid ester, R"CO$_2$R', so that the organic stream is enriched with RCO$_2$H;
   (b) separating the aqueous stream from the RCO$_2$H enriched organic stream;
   (c) contacting the organic stream of (b) with a catalyst to obtain a product carboxylic acid ester, RCO$_2$R', and a second carboxylic acid, R"CO$_2$H;
   (d) separating the product ester, RCO$_2$R', from the second carboxylic acid, R"CO$_2$H;
   (e) esterifying the second carboxylic acid of (d), R"CO$_2$H, to obtain the reactant ester, R"CO$_2$R'; and
   (f) recycling the reactant ester, R"CO$_2$R', of (e) to (a);

wherein R is aliphatic or aromatic, R' is alkyl, and R" is aromatic or aliphatic with at least about 4 carbon atoms.

2. A continuous process for the production of alkyl esters from carboxylic acids comprising:
   (a) contacting an aqueous stream containing a first carboxylic acid, RCO$_2$H, with an organic stream comprising a solvent so that the organic stream is enriched with RCO$_2$H;
   (b) separating the aqueous stream from the RCO$_2$H enriched organic stream;
   (c) contacting the organic stream of (b) with a reactant carboxylic acid ester, R"CO$_2$R', and a catalyst to obtain a product carboxylic acid ester, RCO$_2$R', and a second carboxylic acid, R"CO$_2$H;

(d) separating the product ester, $RCO_2R'$, from the second carboxylic acid, $R''CO_2H$;

(e) esterifying the second carboxylic acid, $R''CO_2H$, of (d) to obtain the reactant ester, $R''CO_2R'$; and (f) recycling the reactant ester, $R''CO_2R'$, of (e) to (c);

wherein R is aliphatic or aromatic, R' is alkyl, R" is aromatic or aliphatic with at least about 5 carbon atoms, (a) and (b) are performed at a temperature of about 0° to 100° C. and a pressure of about 0.01 to 10 atms, (c), (d) and (e) are performed at a temperature of about 50° to 200° C. and a pressure of about 0.001 to 10 atms, and the reactant ester, $R''CO_2R'$, is a solid at the temperature and pressure of (a).

3. A continuous process for the production of alkyl esters from carboxylic acids comprising:

(a) contacting an aqueous stream containing a carboxylic acid, $RCO_2H$, with an organic stream comprising a solvent so that the solvent is enriched with $RCO_2H$;

(b) separating the aqueous stream from the $RCO_2H$ enriched organic stream;

(c) contacting the organic stream of (b) with an ester containing a bifunctional polymer comprising a conventional polymeric backbone of carbon or carbon and at least one of oxygen or nitrogen, wherein said polymer is one having both sulfonic acid and carboxyl pendant functional groups, wherein the carboxyl pendant functional groups comprise R' carboxylic acid esters, to obtain a product carboxylic acid ester, $RCO_2R'$, and an acidified bifunctional polymer having both sulfonic acid and carboxylic acid pendant functional groups;

(d) separating the product ester, $RCO_2R'$, from the bifunctional polymer;

(e) esterifying the bifunctional polymer of (d) to obtain the ester containing bifunctional polymer of (c); and (f) recycling the bifunctional polymer of (e) to (c);

wherein R is aliphatic or aromatic and R' is alkyl.

4. The process of claim 3 wherein the sulfonic acid pendant functional groups of the bifunctional polymer comprise sulfonated phenyls.

5. The process of claim 4 wherein the ratio of carboxyl pendant groups to sulfonated phenyl pendant groups is about 1:1 to 4:1.

6. The process of claim 1 wherein $R''CO_2R'$ is substantially immiscible in water.

7. The process of claim 2 or 3 wherein the solvent is substantially immiscible in water.

8. The process of claim 6 wherein $RCO_2H$ has a $R''CO_2R'/H_2O$ solubility ratio of at least 1.

9. The process of claim 7 wherein $RCO_2H$ has a solvent/$H_2O$ solubility ratio of at least 1.

10. The process of claim 1 wherein the boiling point of $RCO_2R'$ is lower than the boiling point $RCO_2H$, $R''CO_2R'$, and $R''CO_2H$.

11. The process of claim 10 wherein $RCO_2R'$ is separated from $RCO_2H$, $R''CO_2R'$, and $R''CO_2H$ by distillation.

12. The process of claim 2 wherein the boiling point of $RCO_2R'$ is lower than the boiling point of $RCO_2H$, $R''CO_2R'$, $R''CO_2H$ and the solvent.

13. The process of claim 12 wherein $RCO_2R'$ is separated from $RCO_2H$, $R''CO_2R'$, $R''CO_2H$ and the solvent by distillation.

14. The process of claim 1 or 2 wherein $R''CO_2H$ is esterified by an alcohol to obtain $R''CO_2R'$.

15. The process of claim 3 wherein the boiling point of $RCO_2R'$ is lower than the boiling point of $RCO_2H$, the solvent and the bifunctional polymer.

16. The process of claim 15 wherein $RCO_2R'$ is separated from $RCO_2H$, the solvent and the bifunctional polymer by distillation.

17. The process of claim 3 wherein the acidified bifunctional polymer is esterified by an alcohol to obtain the ester containing bifunctional polymer.

18. The process of claim 1, 2 or 3 wherein R' is alkyl, having about 8 or less carbon atoms.

19. The process of claim 18 wherein R' is selected from the group consisting of methyl, ethyl, propyl, butyl and 2-ethylhexyl.

20. The process of claim 1 wherein R" is aliphatic with at least about 5 carbon atoms.

21. The process of claim 2 or 20 wherein R" is alkyl.

22. The process of claim 1 or 2 wherein $R''CO_2R'$ is an octanoic, a benzoic, a lauric or a myristic acid ester.

23. The process of claim 1, 2 or 3 wherein R is aryl, alkyl or alkenyl.

24. The process of claim 23 wherein $RCO_2H$ is acrylic acid, methacrylic acid, an aryl acid having at least 2 acid functions or an alkyl acid with R having about 6 or less carbon atoms.

25. The process of claim 1 or 2 wherein the catalyst is a metal salt.

26. The process of claim 1 or 2 wherein the catalyst is a strong acid having a pKa of about 2.0 or less.

27. The process of claim 26 wherein the catalyst is a water insoluble resin capable of carrying functional groups.

28. The process of claim 27 wherein the catalyst is a phenyl sulfonic acid on polystyrene or a perfluorosulfonic acid polymer.

29. The process of claim 26 wherein the catalyst is $H_2SO_4$.

30. The process of claim 1 or 2 wherein the catalyst is a strong base having a pKa of about 10 or more.

31. The process of claim 1, 2 or 3 wherein the aqueous stream contains about 15 mole % of $RCO_2H$ prior to contacting the aqueous stream with the organic stream.

32. The process of claim 1 or 2 wherein a polymerization inhibitor is present in the organic stream before the organic stream is contacted with the catalyst.

33. The process of claim 3 wherein a polymerization inhibitor is present in the organic stream before the organic stream is contacted with the bifunctional polymer.

34. The process of claim 1 or 3 wherein steps (a) and (b) are performed at a temperature of about 0° to 100° C., and steps (c), (d) and (e) are performed at a temperature of about 50° to 200° C.

35. The process of claim 1 or 3 wherein steps (a) and (b) are performed at a pressure of about 0.01 to 10 atm., and steps (c), (d) and (e) are performed at a pressure of about 0.001 to 10 atm.

36. The process of claim 1 or 2 wherein the molar ratio of the reactant ester, $R''CO_2R'$, to the first carboxylic acid, $RCO_2H$, is about 1:1 to 20:1.

37. The process of claim 36 wherein the ratio of $R''CO_2R'$ to $RCO_2H$ is about 5:1 to 10:1.

38. The process of claim 14 wherein the molar ratio of alcohol to $R''CO_2H$ is about 2:1 to about 30:1.

39. A continuous process for the production of alkyl esters from carboxylic acids comprising:

(a) contacting an aqueous stream containing a first carboxylic acid, $RCO_2H$, with an organic stream comprising a reactant carboxylic acid ester, $R''CO_2R'$, said organic stream being immiscible in water and said acid, $RCO_2H$, having a $R''CO_2R'/H_2O$ solubility ratio of at least 1, so that the organic stream is enriched with $RCO_2H$;

(b) separating the aqueous stream from the $RCO_2H$ enriched organic stream;

(c) contacting the organic stream of (b) with a s strong acidic catalyst, wherein said catalyst is a phenyl sulfonic acid on polystyrene, a perfluorosulfonic acid polymer, wherein said polymer is water insoluble, or $H_2SO_4$, to obtain a product carboxylic acid ester, $RCO_2R'$, and a second carboxylic acid, $R''CO_2H$, the product ester, $RCO_2R'$, having a boiling point lower than the boiling point of the first acid, $RCO_2H$, the reactant ester, $R''CO_2R'$, and the second acid, $R''CO_2H$;

(d) separating the product ester, $RCO_2R'$, from the second acid, $R''CO_2H$, the reactant ester, $R''CO_2R'$, and the first acid, $RCO_2H$, by distillation;

(e) esterifying the second carboxylic acid, $R''COH$, of (d) with an $_2$alcohol to obtain the reactant ester, $R''CO_2R'$, and (f) recycling the reactant ester, $R''CO_2R'$, or (e) to (a);

wherein $RCO_2H$ is acrylic acid, methacrylic acid, an aryl acid having at least 2 acid functions, or an alkyl acid with R having about 6 or less carbon atoms, $R''CO_2R'$ is an octanoic, a benzoic, a lauric, or a myristic acid ester, and R' is methyl, ethyl, propyl, butyl or 2-ethylhexyl.

* * * * *